United States Patent
Sun et al.

(10) Patent No.: US 7,672,732 B2
(45) Date of Patent: Mar. 2, 2010

(54) PORTABLE APPARATUS THAT DELIVERS POWER AND INFORMATION TO IMPLANTABLE DEVICES

(75) Inventors: Mingui Sun, Pittsburgh, PA (US); Robert J. Sclabassi, Pittsburgh, PA (US); Daliang L. Li, Pittsburgh, PA (US); Jun Zhao, Pittsburgh, PA (US); Steven Hackworth, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 502 days.

(21) Appl. No.: 11/693,465

(22) Filed: Mar. 29, 2007

(65) Prior Publication Data

US 2007/0228273 A1 Oct. 4, 2007

Related U.S. Application Data

(60) Provisional application No. 60/788,485, filed on Mar. 31, 2006.

(51) Int. Cl.
*A61N 1/00* (2006.01)
*H04B 1/034* (2006.01)

(52) U.S. Cl. .......................... 607/116; 607/115; 607/61; 607/27; 607/30; 607/33; 607/34; 607/35; 455/95; 455/100; 455/128; 340/333

(58) Field of Classification Search .................. 607/27, 607/29–37, 59–62, 64, 67, 113, 115, 116; 128/869, 870, 876, 902, 903, 202.22; 455/92, 455/95, 100, 106, 127.5, 628, 899; 250/336.1, 250/339.06, 340, 370.04, 393, 395; 340/333
See application file for complete search history.

(56) References Cited

U.S. PATENT DOCUMENTS

| | | | | |
|---|---|---|---|---|
| 6,076,016 | A | * | 6/2000 | Feierbach ................. 607/32 |
| 6,167,310 | A | * | 12/2000 | Grevious .................. 607/32 |
| 6,553,263 | B1 | | 4/2003 | Meadows et al. |
| 6,621,687 | B2 | | 9/2003 | Lewis, Jr. et al. |

(Continued)

OTHER PUBLICATIONS

Heetderks, William J., "RF Powering of Millimeter- and Submillimeter-Sized Neural Prosthetic Implants", IEEE Transactions on Biomedical Engineering, vol. 35, No. 5, May 1988, pp. 323-327.

(Continued)

*Primary Examiner*—Bernard E Souw
(74) *Attorney, Agent, or Firm*—Eckert Seamans Cherin & Mellott, LLP; Philip E. Levy, Esq.

(57) ABSTRACT

An apparatus for powering an implant includes first energy interface elements, a removeably attachable holding device and a first energy source, such as a battery. An energy conversion circuit converts first energy into second energy which is transmitted within the body of the patient to the implant. Also, an apparatus for providing information to an implant that includes first energy interface elements and a housing that includes a processor operatively coupled to the first energy interface elements and an energy source operatively coupled to the processor. The processor is structured to generate an information signal and cause the signal to be transmitted within the body of the patient for delivery to the implant. Associated methods are also provided.

111 Claims, 7 Drawing Sheets

U.S. PATENT DOCUMENTS

| | | | |
|---|---|---|---|
| 6,754,472 | B1 | 6/2004 | Williams et al. |
| 6,846,588 | B2 | 1/2005 | Sarkar |
| 6,847,844 | B2* | 1/2005 | Sun et al. .................... 607/32 |
| 6,955,172 | B2 | 10/2005 | Nelson et al. |
| 7,107,103 | B2* | 9/2006 | Schulman et al. ............. 607/61 |
| 7,228,183 | B2* | 6/2007 | Sun et al. .................... 607/60 |
| 7,463,917 | B2* | 12/2008 | Martinez .................... 600/395 |
| 2007/0007285 | A1* | 1/2007 | Sun et al. .................... 219/772 |
| 2007/0228273 | A1* | 10/2007 | Sun et al. .................... 250/305 |
| 2009/0086893 | A1* | 4/2009 | Boyden et al. ................ 378/44 |

OTHER PUBLICATIONS

Griss et al., "Micromachined Electrodes for Biopotential Measurements", Journal of Microelectromechanical Systems, vol. 10, No. 1, Mar. 2001, pp. 10-16.

Goto et al., "An Implantable Power Supply with an Optically Rechargeable Lithium Battery", IEEE Transactions on Biomedical Engineering, vol. 48, No. 7, Jul. 2001, pp. 830-833.

Ghovanloo et al., "In Vitro and In Vivo Testing of a Wireless Multichannel Stimulating Telemetry Microsystem", Proceedings of the 26th Annual International Conference of the IEEE EMBS, San Francisco, CA, USA, Sep. 1-5, 2004, pp. 4294-4297.

Li et al., "Bio-Inspired Electric Power Delivery Antenna through Volume Conduction", Proc. 31st Northeast Bioengineering Conference, Hoboken, NJ, Apr. 2-3, 2005.

Berger et al., "Brain-Implantable Biomimetic Electronics as the Next Era in Neural Prosthetics", Proceedings of the IEEE, vol. 89, No. 7, Jul. 2001, pp. 993-1012.

Hunter et al., "Medical Devices of the Head, Neck, and Spine", Radiographics, vol. 24, No. 1, pp. 257-285, Jan.-Feb. 2004, pp. 257-285.

Kopparthi et al., "Power Delivery for Remotely Located Microsystems", Region 5 Conference: Annual Technical and Leadership Workshop, Apr. 2004, 31-39.

Mueller et al., "Two Novel Techniques for Enhancing Powering and Control of Multiple Inductively-Powered Biomedical Implants", Proceedings of 1997 IEEE International Symposium on Circuits and Systems, Jun. 1997, 1:289-292.

Murakawa et al., "A Wireless Near-Infrared Energy System for Medical Implants", IEEE Engineering in Medicine and Biology, Nov./Dec. 1999, pp. 70-72.

Lindsey et al., "A New Technique for Transmission of Signals from Implantable Transducers", IEEE Transactions on Biomedical Engineering, vol. 45, No. 5, May 1998, pp. 614-619.

Liu et al., "Implantable Biomimetic Microelectric Design", IEEE Engineering in Medicine and Biology Magazine, Sep./Oct. 2005, pp. 66-74.

Sun et al., "Data Communication Between Brain Implants and Computer", IEEE Transactions of Neural Systems and Rehabilitation Engineering, vol. 11, No. 2, Jun. 2003, pp. 189-192.

Wise, Kensall D., "Silicon Microsystems for Neuroscience and Neural Prostheses", IEEE Engineering in Medicine and Biology Magazine, Sep./Oct. 2005, pp. 22-29.

Ferrel et al., "A Multichannel Ultrasonic Biotelemetry System for Monitoring Marine Animal Behavior at Sea", ISA Transactions: vol. 13 (120-131) 1974.

Clark et al., Medical Instrumentation Application and Design, third edition, John G. Webster, Editor, pp. 183-232.

\* cited by examiner

PORTABLE APPARATUS THAT DELIVERS POWER AND INFORMATION TO IMPLANTABLE DEVICES

CROSS-REFERENCE TO RELATED APPLICATION

This application claims the benefit of U.S. Provisional Application No. 60/788,485, entitled "A Portable Apparatus That Delivers Power and Information to Implantable Devices," which was filed on Mar. 31, 2006, the disclosure of which is incorporated herein by reference.

GOVERNMENT CONTRACT

This work was supported in part under U.S. Army SBIR Contract No. W81XWH-05-C-0047 and NIH Contract No. R01EB002099. The United States government may have certain rights in the invention described herein.

FIELD OF THE INVENTION

The present invention relates to implantable devices, such as cardiac pacemakers and deep brain stimulation devices, and in particular to a portable apparatus that is able to deliver power and information to such implantable devices using, for example, volume conduction or inductive coupling.

BACKGROUND OF THE INVENTION

In recent years, medical implants have made profound changes in medicine. When implanted within various parts of the human body, these devices perform important in vivo functions including diagnosis, monitoring, and disease treatment. It is clear that the line between biology and technology is blurring, and biological tissues and man-made machines are becoming integrated. This trend will have a broad impact on the future practice of medicine.

Although many technical barriers for designing and utilizing implantable devices have been removed, there still exist two significant problems: (1) they require an electrical energy supply, and (2) they often require a data communication link. Since existing designs, some of which are described below, have many drawbacks, these problems are hampering the development of the next-generation implants.

Currently, most implantable devices within the body, such as cardiac pacemakers and deep brain stimulation devices, use non-rechargeable batteries as power supplies. Because the batteries inside an implantable device cannot be replaced easily without surgery, different approaches have been studied to power implantable devices by delivering electrical energy transcutaneously from outside of the human body. In some cases, wire connections across the skin have been utilized. Clearly, this percutaneous design is highly invasive and prone to infection. Various designs using, for example, magnetic inductive coupling, ultrasound, optical coupling, and volume conduction have been reported. In most of these designs, an energy transmitter is carried or worn by the patient. This transmitter couples with an energy receiver inside the body to transmit electrical energy. Although these designs provide power supplies for implantable devices in principle, the external device with cables carried or worn by the patient is often cumbersome and inconvenient in the daily life of patients. Thus, there is a need for a portable, preferably low-cost, and convenient apparatus that may be used as a platform to supply electrical power to and communicate with implantable devices.

SUMMARY OF THE INVENTION

In one embodiment, the invention relates to an apparatus for providing power to a device implanted within the body of a patient that includes one or more first energy interface elements, such as electrodes or coils, a holding device having an energy conversion circuit operatively coupled to the first energy interface elements that is structured to be removeably attached to the exterior of the body of the patient, and a first energy source, such as a battery, operatively associated with the holding device and operatively coupled to the energy conversion circuit. The energy conversion circuit is structured to receive first energy from the first energy source and convert the first energy into second energy which is provided to the one or more first energy interface elements. The one or more first energy interface elements transmit the second energy within the body of the patient, and at least a portion of the second energy is received by one or more second energy interface elements, such as electrodes or coils, associated with the implanted device. The received energy is used to charge a second energy source, such as a battery and/or supercapacitor, of the implanted device.

In one particular embodiment, the first energy DC current that is converted into an AC current (the second energy) by the energy conversion device. Furthermore, the AC current may be transmitted within the body of the patient via electrodes through volume conduction through ionic fluid present in the body of the patient.

In another embodiment, the one or more first energy interface elements include a first coil and the one or more second energy interface elements include a second coil, and the second energy is RF energy. The second energy in the form of the RF energy is radiated by the first coil and transmitted within the body of the patient, wherein the received RF energy induces a current in the second coil that is used to charge the second energy source.

The apparatus may further include an attachment pad, such as a flexible foam pad, structured to be removeably attached to the exterior of the body of the patient, wherein the holding device and the first energy interface elements are attached to the attachment pad, and wherein the first energy source is held by the holding device. The holding device is preferably removeably attached to the attachment pad through a snap connection, and the energy conversion circuit is electrically connected to the first energy interface elements through the snap connection.

The holding device may further include communication circuitry, as a separate element or a part of a processor (also referred to herein as control circuitry), that is operatively coupled to the first energy interface elements for generating an information signal which is provided to the first energy interface elements and transmitted by the first energy interface elements within the body of the patient for delivery to the second energy interface elements for use by the implanted device.

In a particular embodiment, the battery is wirelessly electrically connected to the energy conversion circuit when the battery is fit into the holding device.

The attachment pad may include an adhesive material on an outer surface thereof for removeably attaching the attachment pad to the exterior of the body of the patient. Alternatively, the attachment pad may include a magnetized material, such as a magnetized polymeric material, having a first polarity for removeably attaching the attachment pad to the exterior of the body of the patient by being attracted to a magnetized area of the implanted device, the magnetized area having a second polarity opposite the first polarity. As a further alternative, the attachment pad may include a matrix of spikes provided on an outer surface thereof for removeably attaching the attachment pad to the exterior of the body of the patient by hooking the epidermis of the body of the patient.

The electrodes used in the present invention may have any of a number as shapes, such as those shapes shown in FIGS. 4A-4F. In one particular embodiment, the one or more first energy interface elements include a first circular electrode and second, third and fourth annular electrodes, and the one or more second energy interface elements include a plurality of device electrodes including at least a second circular electrode and a fifth annular electrode. In this embodiment, the second energy transmitted within the body of the patient includes a first current emitted through the first circular electrode and the fourth annular electrode and a second current emitted through the second and third annular electrodes, the second current at least partially blocking a shorting current generated by the apparatus. Preferably, the second and third annular electrodes are located between the first circular electrode and the fourth annular electrode.

In another embodiment, the invention relates to an apparatus for providing information to a device implanted within the body of a patient that includes one or more first energy interface elements and a device housing that includes a processor operatively coupled to the first energy interface elements and an energy source operatively coupled to the processor. The device housing and the first energy interface elements are structured to be removeably attached to the exterior of the body of the patient. In addition, the processor is structured to generate an information signal and cause the first energy interface elements to transmit the information signal within the body of the patient for delivery to one or more second energy interface elements associated with the implanted device. The apparatus may further include an attachment pad structured to be removeably attached to the exterior of the body of the patient, wherein the device housing and the one or more first energy interface elements are attached, preferably removeably attached, to the attachment pad. The information signal may be a modulated energy signal modulated with the information to be provided to the device implanted within the body of a patient as, for example, a plurality of AC current pulses transmitted within the body of the patient through volume conduction. The energy interface elements in this device may be electrode or coils, thus information may be remitted by, for example, volume conduction as just described or inductive coupling.

The processor may be further structured to generate a data acquisition signal and cause the one or more first energy interface elements to transmit the data acquisition signal within the body of the patient, wherein the data acquisition signal is received by the one or more second energy interface elements and causes the implanted device to generate a data signal and cause the one or more second energy interface elements to transmit the data signal within the body of the patient. The data signal is received by the one or more first energy interface elements and provided to the processor.

Also provided is a method of providing power to a device implanted within the body of a patient that includes steps of removeably attaching a pad to the exterior of the body of the patient, wherein the pad has one or more first energy interface elements, providing first energy from a first energy source associated with the pad, converting the first energy into second energy, providing the second energy to the one or more first energy interface elements, transmitting the second energy within the body of the patient through the one or more first energy interface elements, receiving at least a portion of the second energy at one or more second energy interface elements associated with the implanted device, and using the at least a portion of the second energy to charge a second energy source of the device. The method may employ any of the various devices and components just described. In one particular embodiment, the transmitting step comprises transmitting a first current and a second current, wherein the second current at least partially blocks a shorting current that is present during the transmitting step. The method may also further include generating an information signal, providing the information signal to the one or more first energy interface elements, and transmitting the information signal within the body of the patient through the one or more first energy interface elements for delivery to the second energy interface elements for use by the implanted device.

In a further embodiment, the invention provides a method of providing information to a device implanted within the body of a patient including steps of removeably attaching a pad to the body of the patient, wherein the pad has one or more first energy interface elements, generating an information signal using a processor associated with the pad, providing the information signal to the one or more first energy interface elements, transmitting the information signal within the body of the patient through the one or more first energy interface elements (using, for example, volume conduction or inductive coupling), and receiving the information signal at one or more second energy interface elements associated with the implanted device. The method may employ any of the various devices and components just described. The transmitting step may include transmitting a first current and a second current, the second current at least partially blocking a shorting current that is present during the transmitting step.

It is an object of this invention to provide a method and apparatus for conveniently and comfortably providing power to a device that is implanted within the body of a patient.

It is a further object of this invention to provide a method and apparatus for providing power to a device that is implanted within the body of a patient that employs an inexpensive flexible attachment pad that may be removeably attached to the patient's body.

It is still a further object of this invention to provide a method and apparatus for providing power to a device that is implanted within the body of a patient that employs a combination energy source holder/circuit board that may be easily and removeably attached to an attachment pad.

It is still a further object of this invention to provide a method and apparatus for conveniently and comfortably providing information, such as programming information, to a device that is implanted within the body of a patient.

It is still a further object of this invention to provide a method and apparatus for conveniently and comfortably obtaining information from an implanted device.

It is still a further object of this invention to provide a method and apparatus for energizing and delivering information to an implanted device that does not require an invasive procedure.

It is still a further object of this invention to provide a method and apparatus for providing information to a device that is implanted within the body of a patient that employs an inexpensive flexible attachment pad that may be removeably attached to the patient's body.

It is still a further object of this invention to provide a method and apparatus for providing information to an implanted device that employs a housing including a processor, a display and one or more input elements that may be that may be easily and removeably attached to an attachment pad.

It is still a further object of this invention to provide a method and apparatus for providing power and/or information to a device that is implanted within the body of a patient that transmits the power and/or information within the patient's body using, for example, AC current transmitted by volume conduction, RF energy radiated within the body, ultrasonic energy transmitted within the body, optical energy transmitted within the body, or radioactive energy transmitted within the body.

The invention described in the present application may employ technology described in U.S. Pat. No. 6,847,844, entitled "Method of Data Communication with Implanted Device and Associated Apparatus," the disclosure of which is incorporated herein by reference.

As used herein, the term "volume conduction" means data communication by wireless passage of data by current pulses passing through living biological tissues (e.g., through ionic fluid present therein) between an implanted device and an external device.

As used herein, the term "patient" means a member of the animal kingdom, including human beings.

As employed herein, the term "current pulse(s)" means electrical current waveforms which have been modified to carry information such as by, for example, phase shift keying, amplitude modulation or frequency modulation.

Therefore, it should now be apparent that the invention substantially achieves all the above aspects and advantages. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

DESCRIPTION OF THE PREFERRED EMBODIMENTS

Figure 1A:
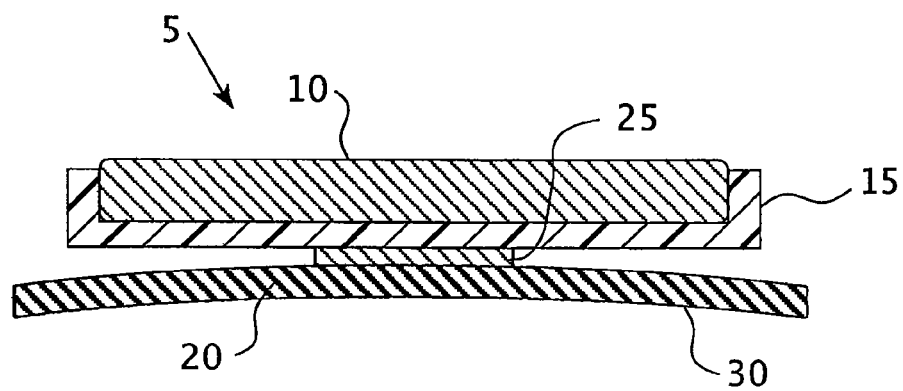
FIG. 1A is a cross-sectional view of an apparatus for providing power to an implantable device according to one embodiment of the present invention.
Figure 1B:
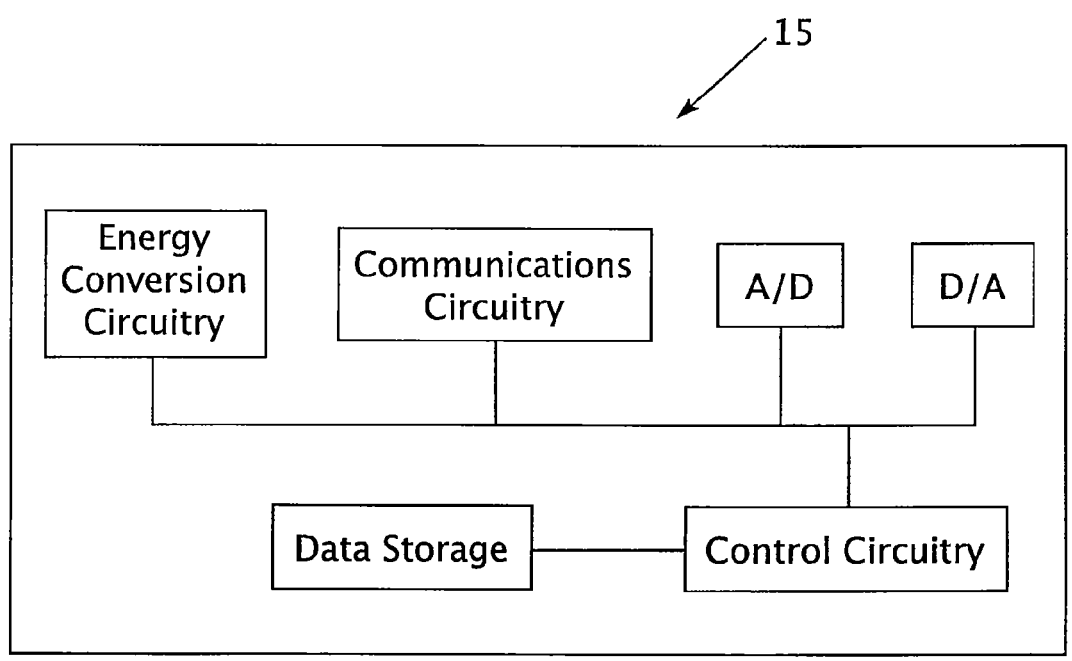
FIG. 1B is a block diagram of one embodiment of the dual-use battery holder/circuit board forming a part of the apparatus shown in FIG. 1A.

FIG. 1A is a cross-sectional view of an apparatus 5 for providing power to an implantable device according to one embodiment of the present invention. The apparatus 5 includes three major components: a thin-profile battery (or battery pack) 10, which may have a disk shape or any other suitable shape, a dual-use battery holder/circuit board 15, and a flexible pad 20, which may be made of foam or some other suitable deformable material. The battery 10, which may be a rechargeable lithium-ion (Li-ion) battery, provides power to: 1) an energy conversion circuit provided on the battery holder/circuit board 15 which, as described herein, delivers energy in, for example and without limitation, an electromagnetic, ultrasonic, optical, radioactive, or ionic current form to an implantable device within the human body, and 2) electronic circuitries also provided on the battery holder/circuit board 15 for communication, data acquisition, and control functions of the apparatus 5. The dual-use battery holder/circuit board 15, preferably made of an insulating synthetic material, preferably has the shape of a shallow baking pan as seen in FIG. 1A, and may be disk-shaped to match the shape of the battery 10. As described above, the dual-use battery holder/circuit board 15 not only holds the battery 10, preferably by a snap fit through forces exerted by the upstanding walls of the dual-use battery holder/circuit board 15, but also bears printed circuit patterns and surface mount technology (SMT) components on both sides of the "pan bottom" which implement the energy conversion, communication, A/D and D/A, data storage, and control circuitry and thereby enable the apparatus 5 to provide such functions. A block diagram of one embodiment of the dual-use battery holder/circuit board 15 showing these components is provided in FIG. 1B.

The flexible pad 20 includes a signal/energy interface element or elements (see FIGS. 2A-9), which transmits energy and/or information signals (data) to, and receives information signals (data) from, the implantable device. The flexible pad 20 may be a disposable component. A snap connector 25 is provided at the center of the top side of the flexible pad 20 to enable the flexible pad 20 to be snap-engaged with the battery holder/circuit board 15. The flexible pad 20, which is adapted to be attached to the skin by, for example, a number of methods described herein, conforms to the curvature of the body surface.

A number of different methods may be utilized to attach the apparatus 5, and in particular the flexible pad 20, to the patient's skin. The choice of method depends on the particular application in question. In one method, the flexible pad 20 is adhered to the skin using a suitable adhesive material, such as a glue, that is provided on the skin contact side 30 of the flexible pad 20. In another method, the flexible pad 20 includes a magnetized material, such as a magnetized polymeric material, which allows attachment to the skin by interfacing with a magnetized area having an opposite magnetic polarity that is provided on the surface of the implantable device being charged. In still another method, the skin contact side 30 of the flexible pad 20 includes an area where a matrix of numerous tiny spikes is formed in a similar fashion as that described in, for example, Sun et al., U.S. Patent Application Ser. No. 60/887,879 entitled "Skin-Screw Electrodes for Super-Fast Installation on Hairy Skin without Using Adhesives and Electrolyte Gel" and owned by the assignee hereof and Griss et al., "Micromachined Electrodes for Biopotential Measurements," Journal of Microelectromechanical Systems, vol. 10, pp. 10-16, 2001. These spikes, in certain shapes and dimensions, hook the outermost layer of the epidermis (stratum corneum) when the flexible pad 20 is pressed on the skin.

Two specific embodiments of the apparatus 5 are described herein which employ volume conduction and magnetic coupling, respectively, for neural devices implanted within or under the patient's skull. The depiction of neural devices implanted within or under the patient's skull is meant to be exemplary, and it should be understood that these embodiments may also be employed in connection with devices implanted in other parts of the human body. In addition, energy (generated by an energy conversion circuit as described herein) may be transmitted within the body in other forms, such as, without limitation, ultrasonic energy or optical energy.

Figure 2:
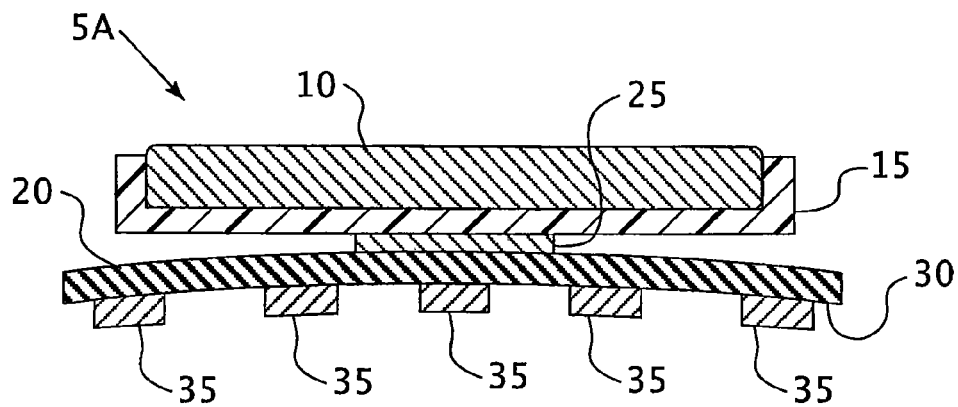
FIGS. 2 and 3A are cross-sectional schematic diagrams of one particular embodiment of the apparatus shown in FIG. 1A which employs volume conduction.
Figure 3A:
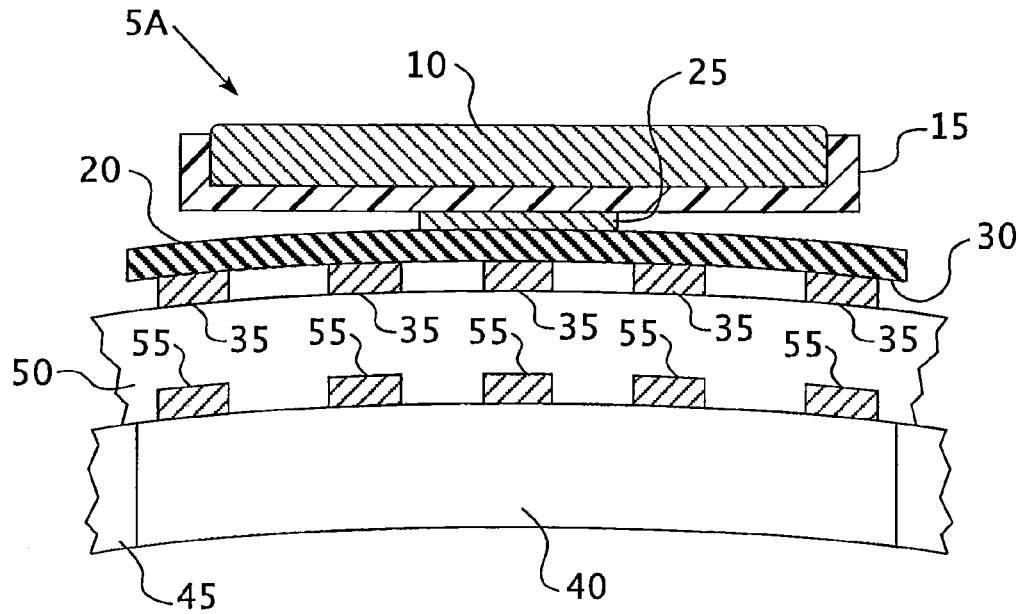

FIGS. 2 and 3A are cross-sectional schematic diagrams of one particular embodiment of the apparatus 5, indicated by the reference numeral 5A, which employs volume conduction. In FIG. 3A, the apparatus 5A is shown as being operatively coupled to a cranial prosthetic neural implant 40 provided within the skull 45 and under the scalp 50 of the patient. Preferably, the apparatus 5A has a size similar to an American quarter and has a thickness of approximately 5 mm. The apparatus 5A includes a battery 10, such as a Li-ion coin battery weighing about 4 grams (equivalent to 3 large paper clips), a battery holder/circuit board 15, which may be made of thin fiber glass, and a flexible pad 20 (similar to an ECG pad) which is snapped on the battery holder/circuit board 15 near the center thereof through a snap connector 25. These components are as described in connection with FIG. 1A. As seen in FIGS. 2 and 3A, the skin contact side 30 of the flexible pad 20 includes an array of electrodes 35 which have both conductive and adhesive areas for skin interfacing. The electrodes 35 are electrically connected to the battery holder/circuit board 15, and in particular to the energy conversion, communication, A/D and D/A, data storage, and control circuitry provided thereon, through the snap connector 25 and form the signal/energy interface element described above in connection with FIG. 1A.

Figure 3B:
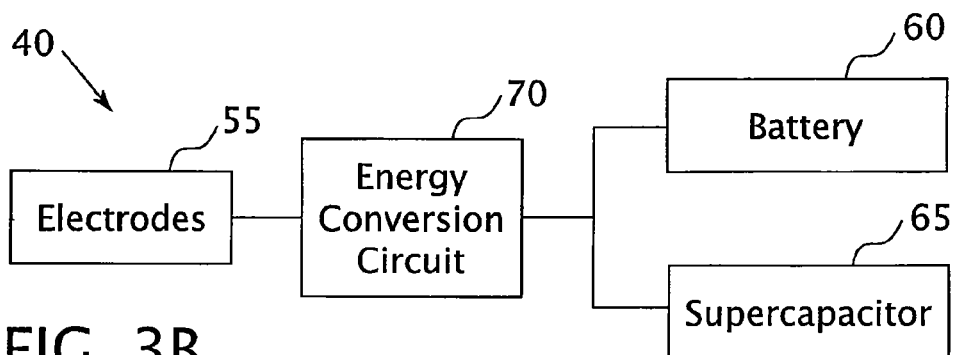
FIG. 3B is a block diagram showing selected components of the implantable device shown in FIG. 3A.

The coupling between the apparatus 5A and a cranial prosthetic neural implant 40 during energy delivery is shown in FIG. 3A. As seen in FIG. 3A, the cranial prosthetic neural implant 40 includes an array of electrodes 55 (acting as energy interface elements) on the surface thereof. In operation, the apparatus 5A is attached to the scalp 50 at a location over the cranial prosthetic neural implant 40, and the electrodes 35 provided on the flexible pad 20 transmit a small amount of electrical current to the scalp 50. Part of the transmitted current is received by the electrodes 55 of the cranial prosthetic neural implant 40. The received current is provided to and charges a combination including a small rechargeable battery 60 and a supercapacitor 65 provided within the cranial prosthetic neural implant 40 as shown in FIG. 3B, which is a block diagram showing selected components of the cranial prosthetic neural implant 40. The use of a supercapacitor 65 in this manner is advantageous as it solves a critical problem associated with small-size Li-ion batteries having relatively high internal impedance that are commonly used. In particular, because a small-size Li-ion battery has a relatively high internal impedance, it cannot adequately produce sharp stimulation pulses which may be required in a particular implantable device application. The supercapacitor 65 provides a better solution by supplying the required power necessary for sharp voltage transitions. In addition, the supercapacitor 65 prolongs the battery life of the cranial prosthetic neural implant 40 and saves energy because it is an energy storage device and a power-regulation circuit is not needed.

Because DC current causes polarization of electrodes such as electrodes 35 and 55, it is preferable to use AC current for energy transmission from the apparatus 5A to the cranial prosthetic neural implant 40. In particular, the battery 10 generates a DC current which is provided to the energy conversion circuitry provided on the battery holder/circuit board 15. The conversion circuitry provided on the battery holder/circuit board 15 converts the received DC current to an AC current in any one of a number of known manners. The AC current is provided to the electrodes 35 which transmit the AC current to the electrodes 55 as described above by volume conduction through the scalp 50. The AC current received by the electrodes 55 is then converted to a DC current by an energy conversion circuit 70 (FIG. 3B), such as a rectifier or a voltage multiplier circuit, that is provided within the cranial prosthetic neural implant 40 and operatively coupled to the battery 60 and the supercapacitor 65. The DC current produced by the energy conversion circuit 70 is used for charging (recharging) the battery 60 and the supercapacitor 65. The frequency of the AC current generated by the apparatus 5A may be selected from a wide range of frequencies; however, frequencies within or close to the biological range (usually below 100 Hz) are preferably avoided. In addition, extremely high frequencies are also preferably avoided due to the increased loss from tissue absorption at these frequencies.

Figure 4A:
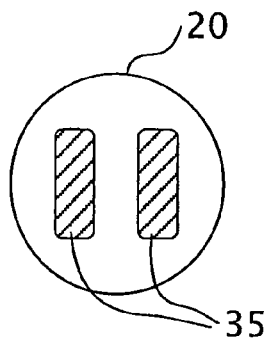
FIGS. 4A through 4F show six different particular shape and pattern embodiments that may be employed for the electrodes provided on the flexible pad of the apparatus shown in FIG. 2.
Figure 4B:
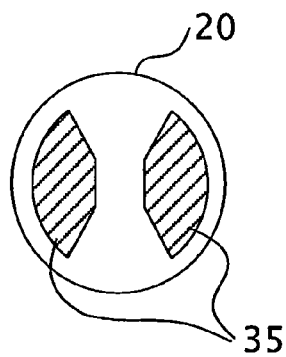
Figure 4C:
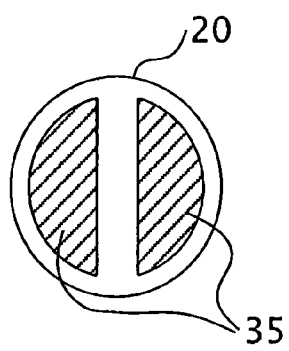
Figure 4D:
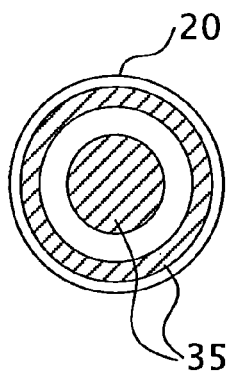
Figure 4E:
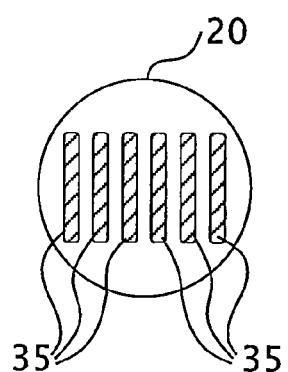
Figure 4F:
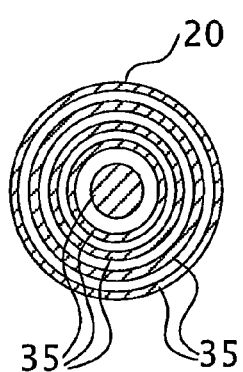
Figure 5:
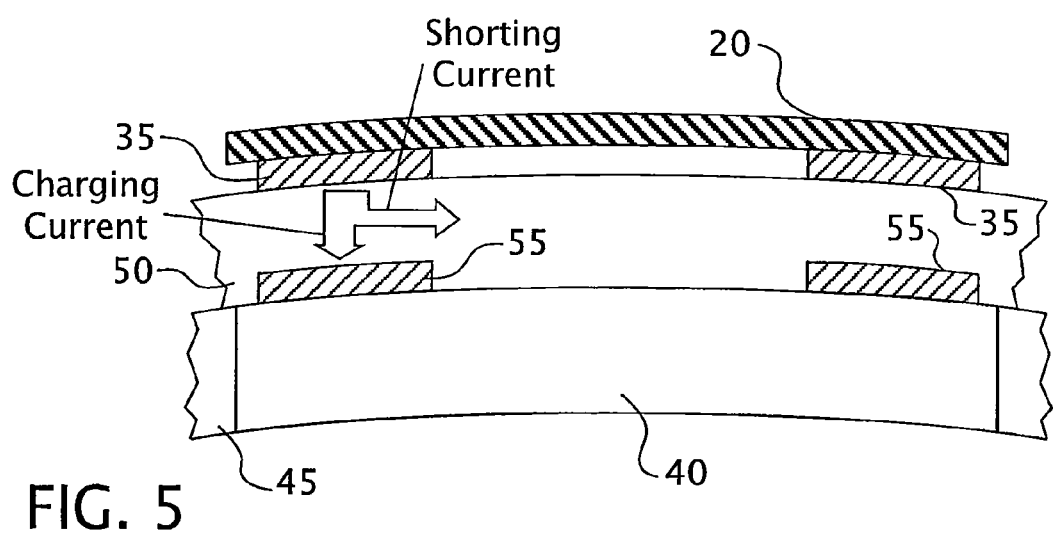
FIG. 5 is a schematic diagram showing the current flowing through the shorting path between the current-emitting electrodes of the apparatus shown in FIG. 2.

A number of different shapes and patterns for the electrodes 35 forming the array provided on the skin surface 30 of the flexible pad 20 are possible. FIGS. 4A through 4F show six different particular shape and pattern embodiments that may be employed in the apparatus 5A (or other embodiment described herein). FIGS. 4A and 4E show substantially rectangular shapes, FIG. 4C shows a substantially semicircular shape, and FIGS. 4D and 4F show substantially annular and semicircular shapes. It should be understood that the particular shape and pattern embodiments shown in FIGS. 4A through 4F are meant to be exemplary and not limiting. Each embodiment shown in FIGS. 4A through 4D contains only two electrodes 35 which together form a current dipole. The particular design shown in FIG. 4B reduces the path between the two electrodes 35 so that the shorting current (described elsewhere herein) can be reduced. However, this design cannot emit large amounts of current because of the high current density in the tissue located in the narrow space between the two electrodes 35. The particular designs shown in FIGS. 4C and 4D, on the other hand, are capable of emitting larger amounts of current but their current transmission efficiency is lower. The particular designs shown in FIGS. 4E and 4F are non-bipolar electrodes which provide deeper tissue penetration. The particular designs shown in FIGS. 4D and 4F have a special rotational symmetry which facilitates placement of the apparatus 5A, since no angular alignment is necessary (as is required with the designs shown in FIGS. 4A, 4B, 4C and 4E). Once the pattern for the array of electrodes 35 is chosen for the apparatus 5A, the same pattern should be chosen for the array of electrodes 55 that is provided on the implantable device (e.g., the cranial prosthetic neural implant 40) to which it is to be coupled to ensure appropriate coupling between these two electrode arrays.

Figure 6A:
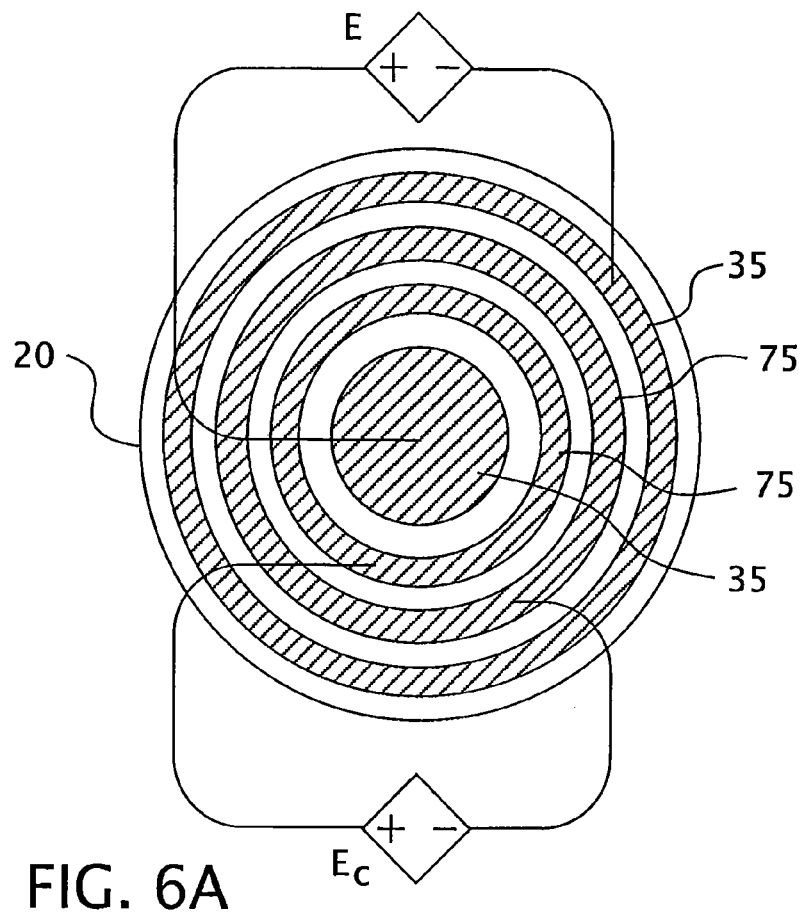
FIG. 6A is a schematic diagram illustrating an active cancellation scheme that may be employed to block the shorting current shown in FIG. 5 by emitting another stream of current through a pair of active cancellation electrodes.

Experiments conducted by the inventors of the present invention have indicated that there is a significant amount of current flowing through the shorting path between current-emitting electrodes 35 of the apparatus 5A. This shorting current, shown in FIG. 5, should preferably be minimized since it causes undesired effects such as heating and loss of efficiency. According to an aspect of a particular embodiment of the present invention, an active cancellation scheme is provided to block the shorting current by emitting another stream of current into the scalp through a pair of active cancellation electrodes 75 which may be provided as shown in FIG. 6A. In order to explain the mechanism of this active cancellation scheme, the volume conduction system provided by the apparatus 5A is approximated using the lumped circuit 80 shown FIG. 6B. In the lumped circuit 80, $E_c$ and E are, respectively, the control voltage for current blocking and the voltage for charging the battery 60 and the supercapacitor 65 provided within the cranial prosthetic neural implant 40 (represented by the dashed box in FIG. 6B), and $R_1$ through $R_5$ are the lumped resistances in different parts of the scalp 50 of the patient. It can be observed that, by adjusting $E_c$, the voltages across $R_2$ and $R_4$ are both reduced, forcing the current produced by E to charge the battery 60 and the supercapacitor 65.

In practice, totally blocking the shorting current may not be desirable since the current across $R_3$ then becomes significant. However, $E_c$ can be adjusted to reach a compromise. Specifically, the charging current across $R_1$ and $R_5$ can be maximized with a constraint that the maximum current density in the entire charging system does not exceed a threshold value. This optimization can be performed either analytically using a circuit model similar to that in the FIG. 6B, or computationally using finite element methods to solve the Poisson's equation numerically.

Figure 7:
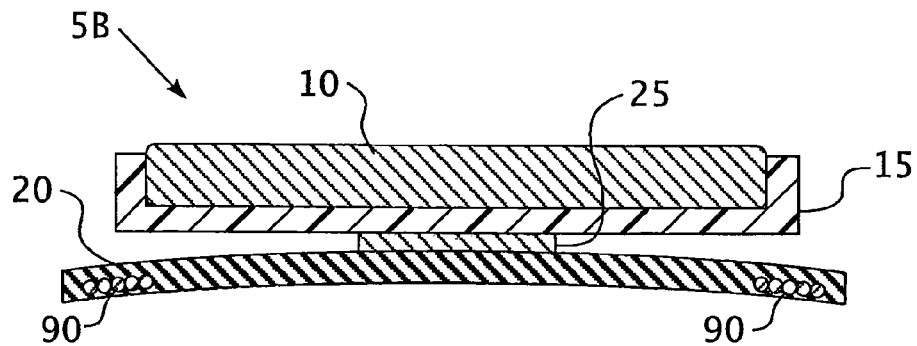
FIGS. 7 and 8 are cross-sectional schematic diagrams of another particular embodiment of the apparatus shown in FIG. 1A which employs radio frequency (RF) magnetic inductive coupling.
Figure 8:
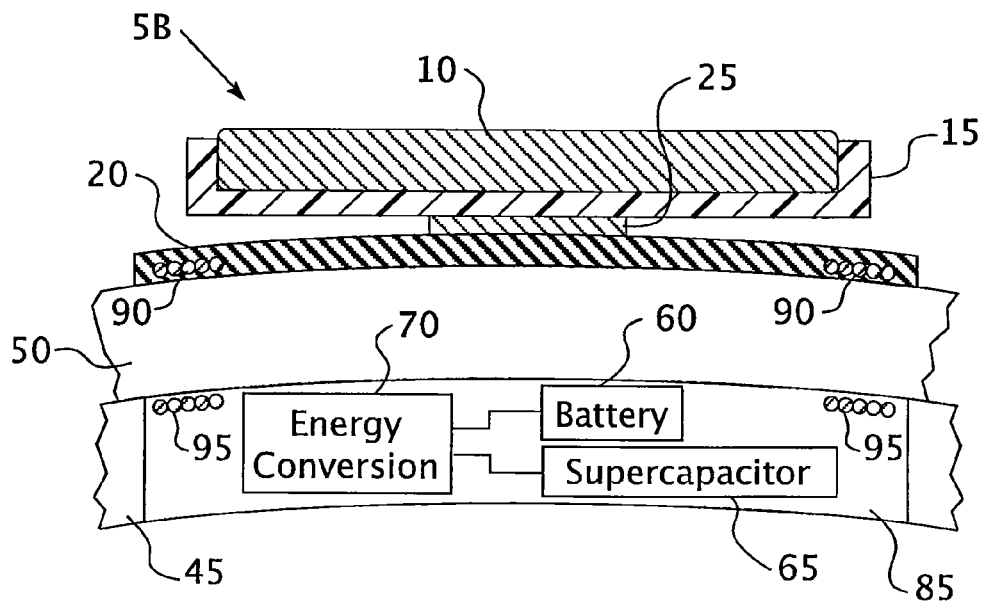
Figure 9:
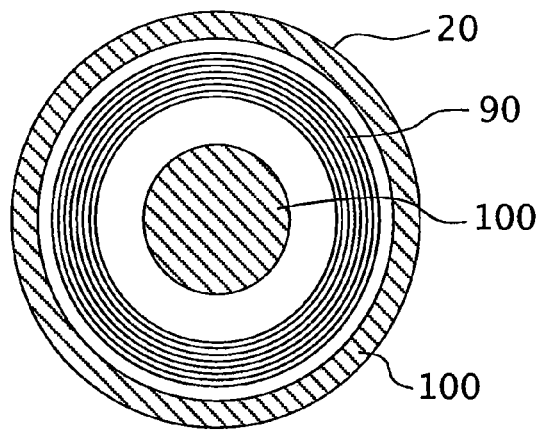
FIG. 9 is a bottom plan view of an embodiment of the flexible pad of the apparatus shown in FIGS. 7 and 8 which employs magnetic strips, adhesive rings, or micro spikes to attach the flexible pad to the skin.

FIGS. 7 and 8 are cross-sectional schematic diagrams of another particular embodiment of the apparatus 5 shown in FIG. 1A, indicated by the reference numeral 5B, which employs radio frequency (RF) magnetic inductive coupling. This method works much like a transformer with two coils inside and outside the human body, where the energy is passed in the form of a magnetic field. In FIG. 8, the apparatus 5B is shown as being operatively coupled to a cranial prosthetic neural implant 85 provided within the skull 45 and under the scalp 50 of the patient. Like the apparatus 5A shown in FIGS. 2 and 3A, the apparatus 5B preferably has a size similar to an American quarter and has a thickness of approximately 5 mm. The apparatus 5B includes a battery 10, such as a Li-ion coin battery weighing about 4 grams (equivalent to 3 large paper clips), a battery holder/circuit board 15, which may be made of thin fiber glass, and a flexible pad 20 (similar to an ECG pad) which is snapped on the battery holder/circuit board 15 near the center thereof through a snap connector 25. These components are substantially as described in connection with FIG. 1A. As seen in FIGS. 7, 8 and 9 (which is a bottom view of the flexible pad 20), the flexible pad 20 includes therein a primary coil 90. The primary coil 90 is electrically connected to the battery holder/circuit board 15, and in particular to the energy conversion, communication, A/D and D/A, data storage, and control circuitry provided thereon, through the snap connector 25 and forms another embodiment of the signal/energy interface element described above in connection with FIG. 1A.

The coupling between the apparatus 5B and a cranial prosthetic neural implant 85 during energy delivery is shown in FIG. 8. As seen in FIG. 8, the cranial prosthetic neural implant 85 includes a secondary coil 95 therein (which acts as an energy interface element). In operation, the apparatus 5B is attached to the scalp 50 at a location over the cranial prosthetic neural implant 85, and an AC signal is provided to the primary coil 90 provided in the flexible pad 20 by the energy conversion circuitry of the battery holder/circuit board 15. In particular, for this purpose, the energy conversion circuitry is provided with an adjustable oscillator that is eclectically connected to the battery 10 and the primary coil 90 which generates the AC signal that is provided to the primary coil 90. In operation, when the AC signal is provided to the primary coil 90, a second AC signal is induced in the secondary coil 95 provided in the cranial prosthetic neural implant 85 as a result of near-field inductive coupling with the primary coil 90. If necessary, coil 90 may be larger than coil 95 to improve coupling. The secondary coil 95 is operatively coupled to an energy conversion circuit 70, such as a rectifier circuit, that is provided within the cranial prosthetic neural implant 85 and operatively coupled to a battery 60 and a supercapacitor 65. The energy conversion circuit 70 converts the received AC signal into a DC current which is used for charging (recharging) the battery 60 and the supercapacitor 65. The advantages of using the supercapacitor 65 are described elsewhere herein. As described previously, magnetic strips, adhesive rings, or micro spikes can be utilized to attach the flexible pad 20 to the skin (strips 100 in FIG. 9).

As described above, the apparatus 5 may be used in connection with neural implant such as the cranial prosthetic neural implants 40 and 85. Use of the apparatus 5 in such a manner would typically require the removal of a small area of hair on the patient's head. Since a favorable location for the skull-based implant is at the top of the head, a small bald area about the size of a quarter or smaller would not usually cause a cosmetic problem. Even if it is a problem for certain people, the area can be concealed easily by a small hair patch. Also, the apparatus 5 typically only needs to be used infrequently (e.g., once per month) at night times for recharging purposes. Due to the low frequency of usage, it will not be a significant factor affecting the life of the patient. Furthermore, the cost of each recharging is projected to be low for (the cost of the disposable flexible pad 20), which should be well affordable by patients. This approach requires the battery 10 on the apparatus 5 to be rechargeable, and it is preferably designed as such.

Figure 10:
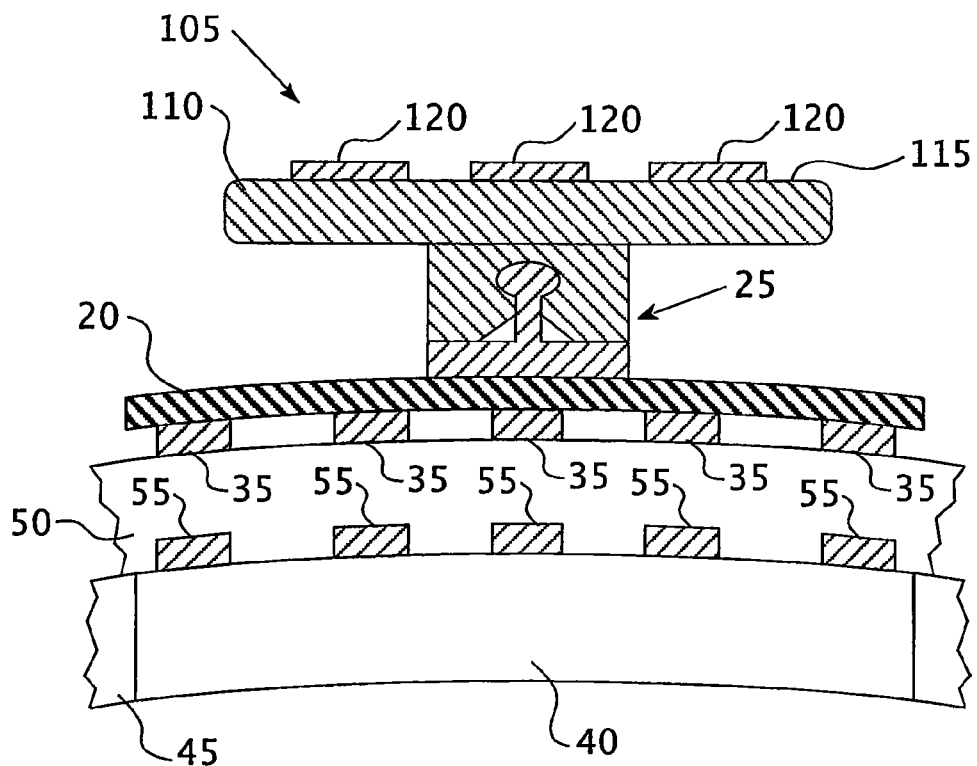
FIG. 10 is a cross-sectional schematic diagram of an apparatus according to an alternate embodiment of the invention which allows for more direct control of an implantable device which employs volume conduction.
Figure 11:
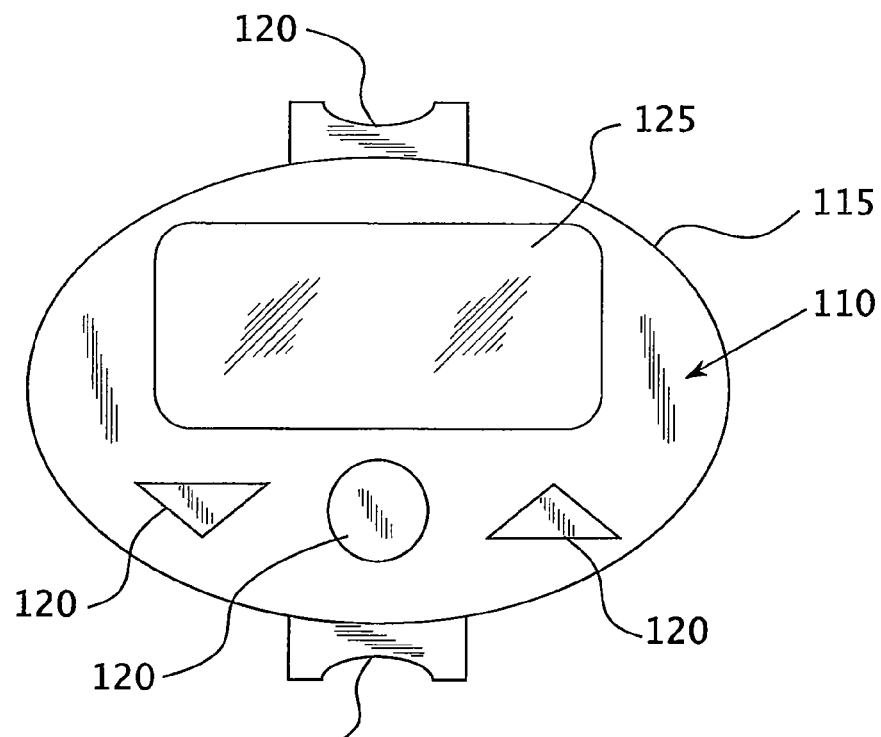
FIG. 11 is a top plan view of one embodiment of the controller device forming a part of the apparatus shown in FIG. 10.

In certain applications, the functions of implantable devices must be controlled by doctors and/or patients. For example, in the case of deep brain stimulation (DBS) devices, the doctor and patient must select a set of parameters to generate appropriate stimulation pulses. Although each apparatus 5, 5A and 5B described previously is capable of performing data acquisition and passing information to an implantable device, such as the cranial prosthetic neural implants 40 and 85, by transmitting data through volume conduction or inductive coupling, an alternate embodiment of the present invention makes this data transmission more convenient by allowing a more direct device control. In particular, FIG. 10 is a cross-sectional schematic diagram of an apparatus 105 according to an alternate embodiment of the invention which allows for more direct device control which employs volume conduction. The apparatus 105 is similar to the apparatus 5A shown in FIGS. 2 and 3 in that it includes a flexible pad 20 having electrodes 35 for transmitting current by volume conduction to electrodes 55 of a device such as a cranial prosthetic neural implant 40. The apparatus 105 also includes a snap connector 25 coupled to the flexible pad 20. However, instead of a battery 10 and a dual-use battery holder/circuit board 15 being connected to the snap connector 25 as is the case with the apparatus 5A, the apparatus 105 includes a controller device 110 that is connected to the snap connector 25. A top plan view of one embodiment of the controller device 110 is shown in FIG. 11. The controller device 110, which may have an oval shape (although other suitable shapes are also possible), includes a housing 115 that includes therein a battery and preferably energy conversion, communication, A/D and D/A, data storage (e.g., flash memory), and a processor/control circuitry (e.g., a microprocessor or microcontroller) (as shown in, for example, FIG. 1B) to enable the apparatus 105 to provide the functionality described herein (one or more of the communication, A/D and D/A circuitry may be provided as part of the processor/control circuitry). In addition, as seen in FIG. 11, the controller device 110 includes several buttons/keys 120 and a display 125, such as an LCD screen, to provide input and output functionality for the apparatus 105. In operation, the doctor or patient can navigate through one or more menus provided on the display and choose, using the buttons/keys 120, the desired functions for the apparatus 105 (including control signal to be sent to the associated implanted device by volume conduction as described elsewhere herein). As will be appreciated, this functionality may be provided through appropriate software/firmware that is provided in the memory of and executable in the processor/control circuitry of the controller device 110.

Once the controller device 110 is programmed (i.e., the desired selections are made as just described), the patient connects it to the flexible pad 20 as shown in FIG. 10 and performs an activation function. For example, the activation function may include squeezing two side buttons 120 simultaneously. When activation occurs, the appropriate data signals are sent to and/or received from the implantable device, such as the cranial prosthetic neural implant 40. Sounds may also be utilized to signal the readiness of the system and the completion of the activated tasks. Data that is received by the controller device 110 from the implantable device may be stored in the data storage component (e.g., flash memory) that is provided within the controller device 110. Such stored data may then be uploaded easily through a standard USB port or the like to another device, such as a hand-held digital device, a regular PC, or a notebook computer. In one particular embodiment, the processor/control circuitry of the controller device 110 is structured to generate a data acquisition signal and cause the energy interface elements of the apparatus 130 (the electrodes 35 or the coil 90 described below) to transmit the data acquisition signal within the body of the patient, wherein the data acquisition signal is received by the energy interface elements (electrodes 55 or coil 95 described below) of the cranial prosthetic neural implant 40 (or 85) and causes the cranial prosthetic neural implant 40 (or 85) to generate a data signal and cause the energy interface elements thereof to transmit the data signal within the body of the patient. The data signal is then received by energy interface elements of the apparatus 130 and provided to the processor/control circuitry of the controller device 110. In addition, the controller device 110 is also able to provide energy to the implantable device, such as the cranial prosthetic neural implant 40, for charging that device as described elsewhere herein.

Figure 12:
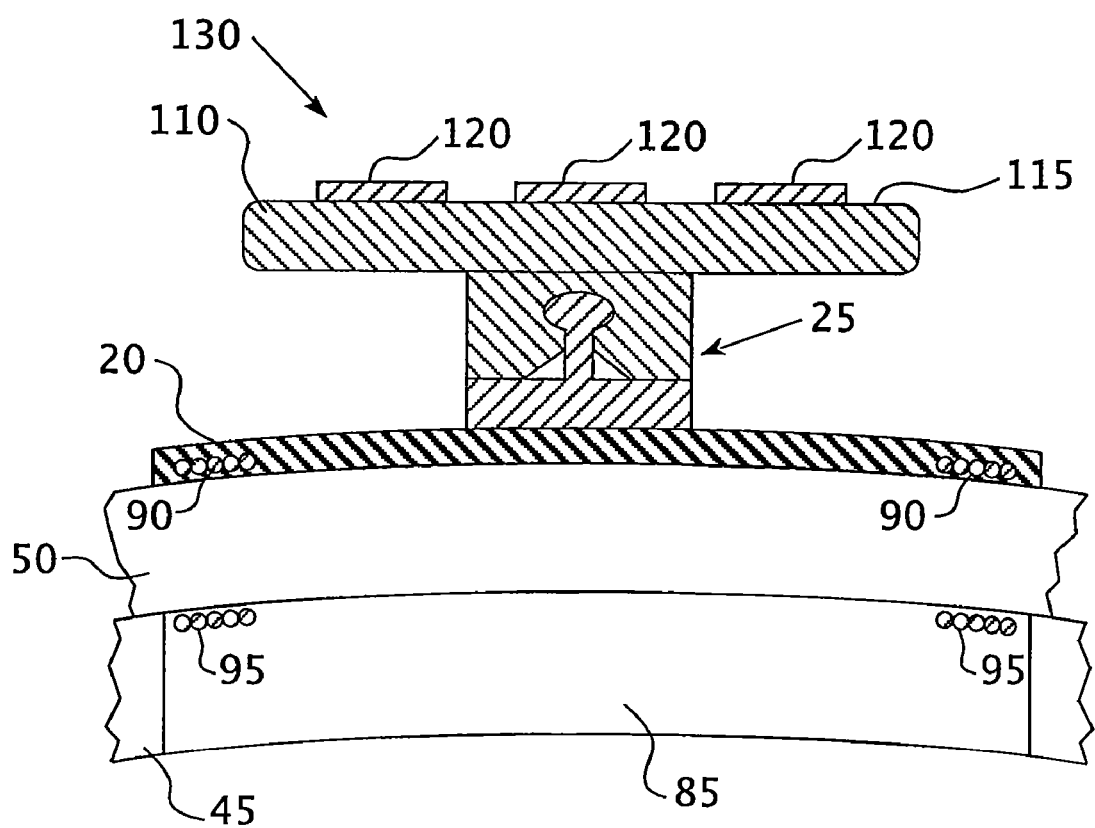
FIG. 12 is a cross-sectional schematic diagram of an apparatus according to an alternate embodiment of the invention which allows for more direct control of an implantable device which employs magnetic coupling.

FIG. 12 is a cross-sectional schematic diagram of an apparatus 130 according to a further alternate embodiment of the invention which is similar to the apparatus 105 but which allows for more direct device control using magnetic coupling instead of volume conduction. In particular, in the case of apparatus 130, information and charging energy is passed between the primary coil 90 of the apparatus 130 and the secondary coil 95 of the cranial prosthetic neural implant 85 by inductive coupling (is Opposed to between the electrodes 35 and 55 by volume conduction in the case of the apparatus 105). Information is preferably transmitted by modulating the RF energy (e.g., to create AC current pulses) with the information to be transmitted using a known or hereafter developed modulation technique. Otherwise, the functioning of the apparatus 130 is substantially identical to the functioning of the apparatus 105. As noted elsewhere herein, modulated ultrasonic and optical energy signals may also be employed.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. An apparatus for providing power to a device implanted within the body of a patient, comprising:
   one or more first energy interface elements;
   a holding device having an energy conversion circuit operatively coupled to said one or more first energy interface elements, said holding device and said one or more first energy interface elements being structured to be removeably attached to the exterior of the body of said patient; and
   a first energy source operatively associated with said holding device, said first energy source being operatively coupled to said energy conversion circuit;
   wherein said energy conversion circuit is structured to receive first energy from said first energy source and convert said first energy into second energy which is provided to said one or more first energy interface elements, wherein said one or more first energy interface elements transmit said second energy within the body of said patient, wherein at least a portion of said second energy is received by one or more second energy interface elements associated with said implanted device and is used to charge a second energy source of said implanted device.

2. The apparatus according to claim 1, further comprising an attachment pad structured to be removeably attached to the exterior of the body of said patient, wherein said holding device and said one or more first energy interface elements are attached to said attachment pad, and wherein said first energy source is held by said holding device.

3. The apparatus according to claim 1, wherein said first energy source is held by said holding device.

4. The apparatus according to claim 1, wherein said second energy comprises AC current, and wherein said AC current is transmitted within the body of said patient through volume conduction.

5. The apparatus according to claim 4, wherein said AC current is transmitted within the body of said patient through ionic fluid present in the body of said patient.

6. The apparatus according to claim 4, wherein said first energy comprises DC current, and wherein said energy conversion circuit converts said DC current into said AC current.

7. The apparatus according to claim 1, wherein said one or more first energy interface elements comprise a plurality of first electrodes and wherein said one or more second energy interface elements comprise a plurality of second electrodes.

8. The apparatus according to claim 4, wherein said one or more first energy interface elements comprise a plurality of first electrodes and wherein said one or more second energy interface elements comprise a plurality of second electrodes.

9. The apparatus according to claim 1, wherein said one or more first energy interface elements comprise a first coil, wherein said one or more second energy interface elements comprise a second coil, wherein said second energy is RF energy, wherein said second energy in the form of said RF energy is radiated by said first coil and transmitted within said body of said patient, wherein said at least a portion of said second energy in the form of at least a portion of said RF energy induces a current in said second coil, and wherein said current is used to charge said second energy source.

10. The apparatus according to claim 1, wherein said second energy is ultrasonic energy.

11. The apparatus according to claim 1, wherein said second energy is optical energy.

12. The apparatus according to claim 2, wherein said holding device is removeably attached to said attachment pad.

13. The apparatus according to claim 12, wherein said holding device is removeably attached to said attachment pad by a snap connection.

14. The apparatus according to claim 13, wherein said energy conversion circuit is electrically connected to said one or more first energy interface elements through said snap connection.

15. The apparatus according to claim 1, wherein said first energy source is a battery.

16. The apparatus according to claim 15, wherein said battery is held by said holding device by being snap fit into said holding device.

17. The apparatus according to claim 15, wherein said battery is fit into said holding device, wherein said holding device has a substantially flat bottom portion and one or more walls extending upwardly from said bottom portion and wherein said one or more walls exert a holding force against said battery when said battery is fit into said holding device.

18. The apparatus according to claim 17, wherein said battery is wirelessly electrically connected to said energy conversion circuit when said battery is fit into said holding device.

19. The apparatus according to claim 17, wherein said battery is a disk shaped battery, and wherein said bottom portion of said holding device is disk shaped.

20. The apparatus according to claim 2, wherein said attachment pad comprises a flexible pad.

21. The apparatus according to claim 20, wherein said attachment pad comprises a flexible foam pad.

22. The apparatus according to claim 2, wherein said attachment pad includes an adhesive material on an outer surface thereof for removeably attaching said attachment pad to the exterior of the body of said patient.

23. The apparatus according to claim 2, wherein said attachment pad includes a magnetized material having a first polarity for removeably attaching said attachment pad to the exterior of the body of said patient by being attracted to a magnetized area of said implanted device, said magnetized area having a second polarity opposite said first polarity.

24. The apparatus according to claim 23, wherein said magnetized material comprises a magnetized polymeric material.

25. The apparatus according to claim 2, wherein said attachment pad includes a matrix of spikes provided on an outer surface thereof for removeably attaching said attachment pad to the exterior of the body of said patient by hooking the epidermis of the body of said patient.

26. The apparatus according to claim 1, wherein said second energy source comprises a rechargeable battery.

27. The apparatus according to claim 1, wherein said second energy source comprises a supercapacitor.

28. The apparatus according to claim 1, wherein said one or more first energy interface elements comprise a first electrode and a second electrode and wherein said one or more second energy interface elements comprise a third electrode and a fourth electrode.

29. The apparatus according to claim 28, wherein said first electrode has a first shape, said second electrode has a second shape, said third electrode has a third shape and said fourth electrode has a fourth shape, and wherein said first shape substantially matches said third shape and said second shape substantially matches said fourth shape.

30. The apparatus according to claim 29, wherein said first, second, third and fourth shapes are substantially rectangular.

31. The apparatus according to claim 29, wherein said first, second, third and fourth shapes are substantially semicircular.

32. The apparatus according to claim 29, wherein said first, second, third and fourth shapes each comprises a four sided shape having a first substantially straight side, and an arcuate side located opposite said first substantially straight side, wherein a first end of said arcuate side is connected to a first end of said first substantially straight side by a second substantially straight side, and wherein a second end of said arcuate side is connected to a second end of said first substantially straight side by a second substantially straight side.

33. The apparatus according to claim 29, wherein said first, second, third and fourth shapes are substantially annular.

34. The apparatus according to claim 28, wherein said first and third electrodes have an annular shape and said second and fourth electrode have a circular shape.

35. The apparatus according to claim 7, wherein each of said first and second electrodes have a substantially rectangular shape.

36. The apparatus according to claim 7, wherein each of said first and second electrodes have a substantially annular shape.

37. The apparatus according to claim 1, wherein said one or more first energy interface elements comprise a first circular electrode and second, third and fourth annular electrodes, and wherein said one or more second energy interface elements comprise a plurality of device electrodes.

38. The apparatus according to claim 37, wherein said device electrodes comprise at least a second circular electrode and a fifth annular electrode.

39. The apparatus according to claim 37, wherein said second energy transmitted within the body of said patient includes a first current emitted through said first circular electrode and said fourth annular electrode and a second current emitted through said second and third annular electrodes, said second current at least partially blocking a shorting current generated by said apparatus.

40. The apparatus according to claim 39, wherein said second and third annular electrodes are located between said first circular electrode and said fourth annular electrode.

41. The apparatus according to claim 1, wherein said holding device further includes communication circuitry operatively coupled to said one or more first energy interface elements for generating an information signal which is provided to said one or more first energy interface elements and transmitted by said one or more first energy interface elements within the body of said patient for delivery to said one or more second energy interface elements for use by said implanted device.

42. The apparatus according to claim 41, wherein said information signal is a modulated energy signal modulated with information to be provided to said implanted device.

43. An apparatus for providing information to a device implanted within the body of a patient, comprising:
one or more first energy interface elements; and
a device housing including a processor operatively coupled to said one or more first energy interface elements and an energy source operatively coupled to said processor, said device housing and said one or more first energy interface elements being structured to be removeably attached to the exterior of the body of said patient;
wherein said processor is structured to generate an information signal and cause said one or more first energy interface elements to transmit said information signal within the body of said patient for delivery to one or more second energy interface elements associated with said implanted device.

44. The apparatus according to claim 43, further comprising an attachment pad structured to be removeably attached to the exterior of the body of said patient, wherein said device housing and said one or more first energy interface elements are attached to said attachment pad.

45. The apparatus according to claim 43, wherein said information signal is a modulated energy signal modulated with the information to be provided to said device implanted within the body of a patient.

46. The apparatus according to claim 45, wherein said modulated energy signal comprises a plurality of AC current pulses.

47. The apparatus according to claim 46, wherein said AC current pulses are transmitted within the body of said patient through volume conduction.

48. The apparatus according to claim 47, wherein said AC current pulses are transmitted within the body of said patient through ionic fluid present in the body of said patient.

49. The apparatus according to claim 46, wherein said one or more first energy interface elements comprise a plurality of first electrodes and wherein said one or more second energy interface elements comprise a plurality of second electrodes.

50. The apparatus according to claim 45, wherein said one or more first energy interface elements comprise a first coil, wherein said one or more second energy interface elements comprise a second coil, wherein said modulated energy signal is a modulated RF energy signal, wherein said modulated energy signal in the form of said modulated RF energy signal is radiated by said first coil, is transmitted within said body of said patient, and induces a current in said second coil.

51. The apparatus according to claim 45, wherein said modulated energy signal is a modulated ultrasonic energy signal.

52. The apparatus according to claim 45, wherein said wherein said modulated energy signal is a modulated optical energy signal.

53. The apparatus according to claim 43, wherein said device housing further includes a display and one or more input elements in electronic communication with said processor.

54. The apparatus according to claim 53, wherein said display comprises an LCD.

55. The apparatus according to claim 53, wherein said input elements comprise one or more keys for inputting data including one or more commands into said processor.

56. The apparatus according to claim 55, wherein said input elements further comprise one or more activation buttons for selectively initiating the transmission of said information signal.

57. The apparatus according to claim 43, wherein said processor is a microprocessor.

58. The apparatus according to claim 43, wherein said processor is a microcontroller.

59. The apparatus according to claim 43, wherein said processor is further structured to generate a data acquisition signal and cause said one or more first energy interface elements to transmit said data acquisition signal within the body of said patient, wherein said data acquisition signal is received by said one or more second energy interface elements and causes said implanted device to generate a data signal and cause said one or more second energy interface elements to transmit said data signal within the body of said patient, and wherein said data signal is received by said one or more first energy interface elements and provided to said processor.

60. The apparatus according to claim 44, wherein said device housing is removeably attached to said attachment pad.

61. The apparatus according to claim 60, wherein said device housing is removeably attached to said attachment pad by a snap connection.

62. The apparatus according to claim 61, wherein said processor is electrically connected to said one or more first energy interface elements through said snap connection.

63. The apparatus according to claim 43, wherein said energy source is a battery.

64. The apparatus according to claim 44, wherein said attachment pad comprises a flexible pad.

65. The apparatus according to claim 64, wherein said attachment pad comprises a flexible foam pad.

66. The apparatus according to claim 44, wherein said attachment pad includes an adhesive material on an outer surface thereof for removeably attaching said attachment pad to the exterior of the body of said patient.

67. The apparatus according to claim 44, wherein said attachment pad includes a magnetized material having a first polarity for removeably attaching said attachment pad to the exterior of the body of said patient by being attracted to a magnetized area of said implanted device, said magnetized area having a second polarity opposite said first polarity.

68. The apparatus according to claim 67, wherein said magnetized material comprises a magnetized polymeric material.

69. The apparatus according to claim 44, wherein said attachment pad includes a matrix of spikes provided on an outer surface thereof for removeably attaching said attachment pad to the exterior of the body of said patient by hooking the epidermis of the body of said patient.

70. The apparatus according to claim 43, wherein said one or more first energy interface elements comprise a first electrode and a second electrode and wherein said one or more second energy interface elements comprise a third electrode and a fourth electrode.

71. The apparatus according to claim 70, wherein said first electrode has a first shape, said second electrode has a second shape, said third electrode has a third shape and said fourth electrode has a fourth shape, and wherein said first shape substantially matches said third shape and said second shape substantially matches said fourth shape.

72. The apparatus according to claim 71, wherein said first, second, third and fourth shapes are substantially rectangular.

73. The apparatus according to claim 71, wherein said first, second, third and fourth shapes are substantially semicircular.

74. The apparatus according to claim 71, wherein said first, second, third and fourth shapes each comprises a four sided shape having a first substantially straight side, and an arcuate side located opposite said first substantially straight side, wherein a first end of said arcuate side is connected to a first end of said first substantially straight side by a second substantially straight side, and wherein a second end of said arcuate side is connected to a second end of said first substantially straight side by a second substantially straight side.

75. The apparatus according to claim 71, wherein said first, second, third and fourth shapes are substantially annular.

76. The apparatus according to claim 70, wherein said first and third electrode have an annular shape and said second and fourth electrode have a circular shape.

77. The apparatus according to claim 49, wherein each of said first and second electrodes have a substantially rectangular shape.

78. The apparatus according to claim 49, wherein each of said first and second electrodes have a substantially annular shape.

79. The apparatus according to claim 43, wherein said one or more first energy interface elements comprise a first circular electrode and second, third and fourth annular electrodes, and wherein said one or more second energy interface elements comprise a plurality of device electrodes.

80. The apparatus according to claim 79, wherein said device electrodes comprise at least a second circular electrode and a fifth annular electrode.

81. The apparatus according to claim 79, wherein said information signal transmitted within the body of said patient includes a first current emitted through said first circular electrode and said fourth annular electrode and a second current emitted through said second and third annular electrodes, said second current at least partially blocking a shorting current generated by said apparatus.

82. The apparatus according to claim 81, wherein said second and third annular electrodes are located between said first circular electrode and said fourth annular electrode.

83. A method of providing power to a device implanted within the body of a patient, comprising:
removeably attaching a pad to the exterior of the body of said patient, said pad having one or more first energy interface elements;
providing first energy from a first energy source associated with said pad;
converting said first energy into second energy;
providing said second energy to said one or more first energy interface elements;
transmitting said second energy within the body of said patient through said one or more first energy interface elements;
receiving at least a portion of said second energy at one or more second energy interface elements associated with said implanted device; and
using said at least a portion of said second energy to charge a second energy source of said device.

84. The method according to claim 83, wherein said second energy comprises AC current, and wherein transmitting step comprises transmitting said AC current within the body of said patient through volume conduction.

85. The method according to claim 84, wherein said AC current is transmitted within the body of said patient through ionic fluid present in the body of said patient.

86. The method according to claim 84, wherein said first energy comprises DC current, and wherein said converting step comprises converting said DC current into said AC current.

87. The method according to claim 83, wherein said one or more first energy interface elements comprise a first coil, wherein said one or more second energy interface elements comprise a second coil, wherein said second energy is RF energy, wherein said transmitting step comprises radiating said RF energy by said first coil, wherein said at least a portion of said second energy in the form of at least a portion of said RF energy induces a current in said second coil, and wherein said using step comprises using said current to charge said second energy source.

88. The method according to claim 83, wherein said second energy is ultrasonic energy.

89. The method according to claim 83, wherein said second energy is optical energy.

90. The method according to claim 83, wherein said energy source is a battery.

91. The method according to claim 83, further comprising removeably attaching said energy source to said pad.

92. The method according to claim 83, wherein said attachment pad comprises a flexible pad.

93. The method according to claim 92, wherein said attachment pad comprises a flexible foam pad.

94. The method according to claim 83, wherein said removeably attaching step comprises removeably attaching said pad using an adhesive material provided on an outer surface of said pad.

95. The method according to claim 83, wherein said removeably attaching step comprises removeably attaching said pad using a magnetized material having a first polarity provided with said pad, said magnetized material being attracted to a magnetized area of said implanted device, said magnetized area having a second polarity opposite said first polarity.

96. The method according to claim 83, wherein said removeably attaching step comprises removeably attaching said pad using a matrix of spikes provided on an outer surface of said pad by hooking the epidermis of the body of said patient with said spikes.

97. The method according to claim 83, wherein said transmitting step comprises transmitting a first current and a second current, said second current at least partially blocking a shorting current that is present during said transmitting step.

98. The method according to claim 83, further comprising generating an information signal, providing said information signal to said one or more first energy interface elements, and transmitting said information signal within the body of said patient through said one or more first energy interface elements for delivery to said second energy interface elements for use by said implanted device.

99. A method of providing information to a device implanted within the body of a patient, comprising:
removeably attaching a pad to the body of said patient, said pad having one or more first energy interface elements;
generating an information signal using a processor associated with said pad;
providing said information signal to said one or more first energy interface elements;
transmitting said information signal within the body of said patient through said one or more first energy interface elements; and
receiving said information signal at one or more second energy interface elements associated with said implanted device.

100. The method according to claim 99, wherein said information signal comprises a modulated energy signal modulated with the information to be provided to said implanted device.

101. The method according to claim 100, wherein said modulated energy signal comprises a plurality of AC current pulses and wherein transmitting step comprises transmitting said AC current pulses within the body of said patient through volume conduction.

102. The method according to claim 100, wherein said one or more first energy interface elements comprise a first coil, wherein said one or more second energy interface elements comprise a second coil, wherein said modulated energy signal is a modulated RF energy signal, wherein said transmitting step comprises radiating said modulated RF energy signal by said first coil, wherein said radiated modulated RF energy signal induces a current in said second coil.

103. The method according to claim 100, wherein said modulated energy signal is a modulated ultrasonic energy signal.

104. The method according to claim 100, wherein said modulated energy signal is a modulated optical energy signal.

105. The method according to claim 99, further comprising removeably attaching said processor to said pad.

106. The method according to claim 99, wherein said pad comprises a flexible pad.

107. The method according to claim 106, wherein said pad comprises a flexible foam pad.

108. The method according to claim 99, wherein said removeably attaching step comprises removeably attaching said pad using an adhesive material provided on an outer surface of said pad.

109. The method according to claim 99, wherein said removeably attaching step comprises removeably attaching said pad using a magnetized material having a first polarity provided with said pad, said magnetized material being attracted to a magnetized area of said implanted device, said magnetized area having a second polarity opposite said first polarity.

110. The method according to claim 99, wherein said removeably attaching step comprises removeably attaching said pad using a matrix of spikes provided on an outer surface of said pad by hooking the epidermis of the body of said patient with said spikes.

111. The method according to claim 99, wherein said transmitting step comprises transmitting a first current and a second current, said second current at least partially blocking a shorting current that is present during said transmitting step.

\* \* \* \* \*

UNITED STATES PATENT AND TRADEMARK OFFICE
CERTIFICATE OF CORRECTION

PATENT NO. : 7,672,732 B2  
APPLICATION NO. : 11/693465  
DATED : March 2, 2010  
INVENTOR(S) : Mingui Sun et al.

Page 1 of 1

Figure 6B:
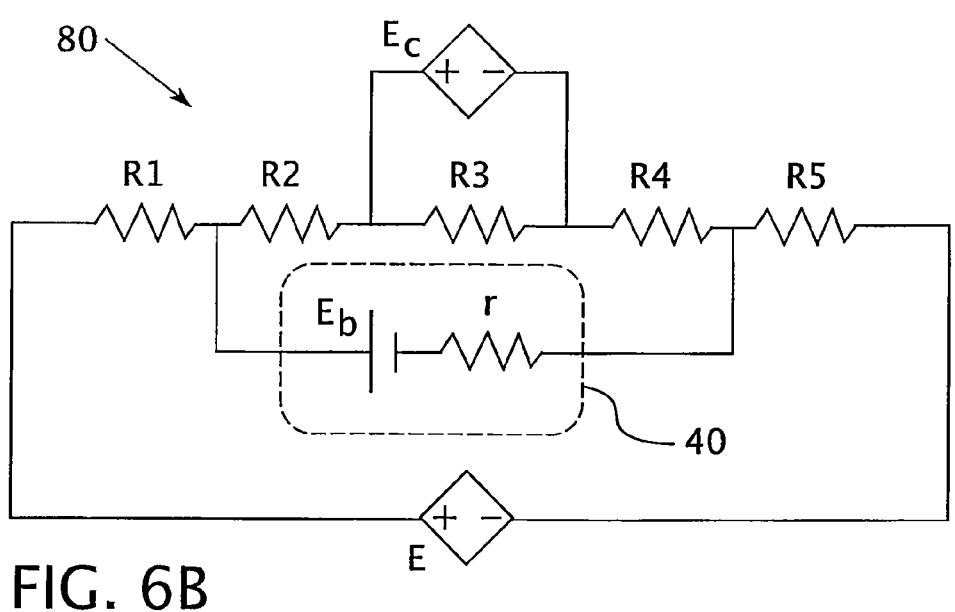
FIG. 6B is a lumped circuit which approximates the volume conduction system shown in FIG. 2 which helps to explain the active cancellation scheme shown FIG. 6A.

It is certified that error appears in the above-identified patent and that said Letters Patent is hereby corrected as shown below:

Column 2, line 24, "that is converted" should read --is converted--.
Column 4, line 64, delete "may be that".
Column 7, line 46, "fiber glass" should read --fiberglass--.
Column 9, line 25, "80 shown FIG. 6B" should read --80 as shown in FIG. 6B--.
Column 9, line 59, "fiber glass" should read --fiberglass--.
Column 12, line 9, "is Opposed" should read --as opposed--.
Column 14, line 14, Claim 34 "electrode" should read --electrodes--.
Column 15, line 60, Claim 52, delete "wherein said".
Column 17, line 6, Claim 74, "comprises" should read --comprise--.
Column 17, line 17, Claim 76, "electrode" should read --electrodes--.
Column 17, line 18, Claim 76, "electrode" should read --electrodes--.

Signed and Sealed this

Eighth Day of June, 2010

David J. Kappos
*Director of the United States Patent and Trademark Office*